United States Patent [19]
Binder

[11] Patent Number: 6,032,071
[45] Date of Patent: Feb. 29, 2000

[54] SKIN EXAMINATION DEVICE

[75] Inventor: Michael Binder, Vienna, Austria

[73] Assignee: Norbert Artner, Vienna, Austria

[21] Appl. No.: 08/849,439

[22] PCT Filed: Nov. 28, 1995

[86] PCT No.: PCT/AT95/00231

§ 371 Date: May 30, 1997

§ 102(e) Date: May 30, 1997

[87] PCT Pub. No.: WO96/16698

PCT Pub. Date: Jun. 6, 1996

[30]     Foreign Application Priority Data

Dec. 1, 1994 [AT]  Austria ................................. 2233/94

[51] Int. Cl.[7] .................................................. A61B 5/00
[52] U.S. Cl. .............................. 600/476; 356/369; 606/9
[58] Field of Search ........................... 600/473, 476,
              600/407, 408; 606/9, 10; 356/369; 382/128;
              128/922, 925

[56]            References Cited

U.S. PATENT DOCUMENTS

| | | |
|---|---|---|
| 4,398,541 | 8/1983 | Pugliese . |
| 4,556,057 | 12/1985 | Hiruma et al. . |
| 4,693,255 | 9/1987 | Beall . |
| 4,768,513 | 9/1988 | Suzuki . |
| 4,930,872 | 6/1990 | Convery . |
| 5,054,502 | 10/1991 | Courage . |
| 5,146,923 | 9/1992 | Dhawan . |
| 5,198,875 | 3/1993 | Bazin . |
| 5,363,854 | 11/1994 | Martens et al. . |
| 5,596,992 | 1/1997 | Haaland et al. . |
| 5,647,368 | 7/1997 | Zeng et al. . |
| 5,653,706 | 8/1997 | Zavislan et al. . |
| 5,701,902 | 12/1997 | Vari et al. . |
| 5,734,739 | 3/1998 | Sheehan et al. . |
| 5,735,276 | 4/1998 | Lemelson . |
| 5,742,392 | 4/1998 | Anderson et al. . |
| 5,769,076 | 6/1998 | Maekawa et al. . |
| 5,835,620 | 11/1998 | Kaplan et al. . |
| 5,836,877 | 11/1998 | Zavislan . |
| 5,842,995 | 12/1998 | Mahadevan-Jansen et al. . |
| 5,848,177 | 12/1998 | Bauer et al. . |
| 5,851,181 | 12/1998 | Talmor . |
| 5,860,967 | 1/1999 | Zavislan et al. . |

FOREIGN PATENT DOCUMENTS

| | | |
|---|---|---|
| 0 475 803 A1 | 3/1992 | European Pat. Off. . |
| 2 658 410 | 8/1991 | France . |
| 94 17 828 U | 12/1994 | Germany . |

*Primary Examiner*—Marvin M. Lateef
*Assistant Examiner*—Shawna J Shaw
*Attorney, Agent, or Firm*—Townsend and Townsend and Crew LLP

[57]            ABSTRACT

A device for optical examination of human skin and its pigmentation comprises a cylindrical housing in which are arranged an optical observation device and a vertical illumination device. Where it faces the skin the housing is delimited by a plate made of transparent plastics or glass, which is applied to a skin site to be examined without introducing an immersion fluid. Light polarization devices are situated between the illumination device and the transparent plate and between the transparent plate and the optical observation device, their degree of polarization being controlled or, optionally, their location being movable mechanically into or out of particular light beam paths.

32 Claims, 10 Drawing Sheets

SKIN EXAMINATION DEVICE

BACKGROUND OF THE INVENTION

The optical examination of skin, which is observed in possibly oblique incident light, either with the naked eye, or using a magnifying glass or microscope, or with a photographic camera, is a well-known and as such well-developed technique. For example, epiluminescence microscopy (ELM) of pigmented lesions of the skin is nowadays a well-established method for the early detection of skin cancer, also for the differential diagnosis of pigmented skin lesions.

The physical-optical principle used here is simple: The skin, or a pigmented skin lesion, is observed using a device having a 4-to 10-fold magnification, such as a magnifying glass device or an operating microscope. The observed area is illuminated by a light source which is usually directed at least substantially orthogonally onto the surface of the skin. In order to be able to make use of the effect of ELM, a plane glass surface is introduced between the magnifying glass device and the surface of the skin. A few drops of immersion fluid, usually oil, are applied between the glass surface and the skin surface. This technique reduces the amount of light diffusely reflected from the ordinarily rough skin surface, and the observer is able to see down to the boundary zone between the epidermis and dermis. The pathological process of pigmented lesions is localized at this boundary zone, the so-called dermo-epidermal junction zone, as well as in the adjacent zones, such as in the epidermis or in superficial layers of the dermis.

By using ELK, a trained dermatologist can therefore gain a more accurate view of the anatomy of pigmented lesions and thus distinguish at a much earlier date between malignant and benign lesions.

A large number of international publications confirm the beneficial effect of ELM in the early diagnosis of malignant skin melanomas.

As has been found in practice, in addition to the above-mentioned, undoubtedly positive effects, the traditional method of epiluminescence microscopy (incident light microscopy) which has just been described possesses in particular the following disadvantages:

Up until now, ELM has been carried out with hand-held magnifying glasses or operating microscopes. Documentation and discussion of the resulting images is rendered difficult as a result and requires the use of a cumbersome archiving and documentation infrastructure.

By applying immersion oil to the skin and under the described glass plate, inclusions of air usually occur, and these render diagnosis more difficult.

An unconventional photographic method, which itself embodies a number of disadvantages, is still used for the—understandably very important—documentation of pigmented lesions.

The photographic process cannot be immediately evaluated and in addition it is always necessary to make a series of exposures.

The photographic process is not standardized; mention should be made here, for example, of the variability in the film material and the variability of the wet development process, because of which the results obtained are not comparable with each other, at least as regards assessment of gray scale or color.

The photographic process can only be used for comparative examinations if additional auxiliary devices such as slide projectors are employed.

The task of selecting and archiving photographic materials involves a relatively high degree of effort and expense.

Summarizing, therefore, it can be stated that the procedure currently used to examine and assess pigmented skin lesions is efficient, but suffers from many disruptive and cost-related factors.

SUMMARY OF THE INVENTION

It is the purpose of the invention to create examination and image-recording facilities for human skin which meet modern requirements, to improve the methods of examination, including the image-recording technique itself, and thus to provide a diagnostic and documentation technique which makes use of all modern principles. This should not only significantly improve the efficiency of ELM in performing skin examinations in general, and specifically in the early diagnosis of pigmented skin lesions, but it should also significantly reduce the amount of manipulation required and the maintenance costs, particularly also as regards the diagnosis and documentation system.

In order to elucidate the path which leads to the invention, reference will be made right away to the drawing and the precise explanation thereof, both of which are dealt with further below. The following remarks can be made:

Within the framework of the general physical theories of epiluminescence microscopy, FIG. 1 shows in diagrammatic form the customary observation of the skin without using ELM techniques. Said FIG. 1 depicts a general view of a highly enlarged vertical section through human skin. The black filled-in circles represent the pigment cells. The arrangement of these pigment cells is characteristic of the disease process in pigmented skin lesions.

Three important boundary layers exist here: a) the boundary layer between the air and the stratum corneum; b) the boundary layer between the epidermis and dermis; c) the boundary layer between the pigmented cells in the skin and their surrounding medium. The thickness of the epidermis is between 0.1 and 0.3 mm.

A light beam (a) is directed onto the skin. Most of this light beam is diffusely reflected at the uppermost boundary layer between the air and the stratum corneum—this is symbolically represented as light beam (r). A much smaller amount of light is reflected from the other deeper-lying boundary layers. The largest amount of incident light (a) is absorbed in the upper parts of the dermis.

FIG. 1 shows clearly that without the use of ELM techniques it is therefore practically impossible to look into the epidermis because most of the light is reflected and exceeds in quantity the amount of penetrating light, of which again only a little is reflected, If the skin is to be examined using conventional ELM techniques, a plane glass surface must be applied and a drop of immersion oil must be introduced between the glass and the surface of the skin, and said oil reduces the amount of diffusely reflected light at the uppermost boundary layer. It is now possible to perceive relatively more light from the deeper-lying pairs. The disadvantage of this method is, in particular, that the surface of the skin has to be wetted with oil. Also disruptive air bubbles are formed in the oil film, thereby causing new and optically disruptive boundary layers to form between thin and dense media.

An attempt has now been made to provide a device for optically examining human skin, in particular skin lesions, said device being uncomplicated and simple for the examining physician to use. The device satisfies modern requirements and is particularly suitable for modern diagnostic and documentation techniques. It has virtually no effect on the patient and his or her state of health. In connection herewith, the aim was also to avoid the use of the disruptive material element required for observation, namely the immersion oil and its application to the skin under the transparent plate, and to achieve the fundamental goal of eliminating the disruptive, diffuse principal portion of the light reflected from the outermost surface of the skin by choosing a fundamentally different method, ideally by making use of a non-material physical phenomenon.

Various theoretical considerations and series of comparative tests culminated in the result that this fundamental goal, including further embodiments, can be achieved with surprising success by changing to the active and/or passive use of polarized light for the skin examination and diagnostic technique.

Accordingly, the subject of the present invention is a now device for the optical examination of human skin.

At this point, it should be stated that very large numbers of surface examinations and analyses are carried out using polarized light and polarization filters. As far as the use of this technique and the devices proposed therefor are concerned, reference is made in particular to U.S. Pat. No. 5,198,875.

The disadvantage of using the state-of-the-art devices, which are open towards the skin side, is that it is not possible to obtain an image of a skin site that is actually reproducible at each examination within an examination series comprising a sequence of examination sessions; this is because it is not possible to achieve a three-dimensional reproductive topography of the skin site which is identical from examination date to examination date, although this is the only way to perform effective comparative examinations. Reproducible and comparative images can be obtained at different points in time only by "flattening" the skin. Such flattening can be accomplished by means of a glass plate, which, however—see above—requires the use of an immersion oil.

Essentially similar disadvantages are exhibited by the skin observation device described in DE 94 17 828 U1, which is intended only for verifying skin care measures. The device in question is easy to handle and has a tubular housing section with a light inlet opening. Between this opening and a light source is fixed a polaroid filter as well as a CCD sensor camera. A hollow handle section projecting at an angle from the housing section accommodates a mechanism for displacing a second polaroid filter also with non-adjustable polarization characteristics. This device is not suitable for serious examination of human skin.

It should be added that a magnifying glass, stereo viewer, microscope or the lens thereof are used as the enlarging devices; the illumination device may comprise, among other things, light-path-modifying, light-focusing and/or light-distributing elements; and the two polarizing devices, i.e. the polarizer and the analyzer, can be adjusted separately from each other, When the skin is examined using the new examination device according to the invention, using a polarization filter, or similar device, without any immersion oil, the following situation arises: Light impinges on the surface of the skin. The amount of light reflected from the first boundary layer accordingly has a linear polarization and can be filtered out when the polarization plane of a polarization filter or analyzer is suitably ("perpendicularly") adjusted—in front of the lens plane of a magnifying glass or a microscope. This makes it possible to obtain the ELM effect without using an immersion oil. By rotating the analyzer, it is possible to obtain both types of display during one and the same examination session, namely on the one hand a purely conventional magnifying glass display for assessing the surface, when the polarization filter is not rotated, and on the other hand the ELM display requiring the use of an immersion fluid (but without such fluid). This method still does not permit any relative increase in the visibility of the melanin pigment because only a polarization filter is used. For routine applications, this principle of using the analyzer has proved advantageous, because a relatively large amount of light is available for observing a skin site, e.g. a pigmented lesion.

This method which is made possible with the new device has a much higher information content. With it the skin is observed using polarized incident light, and the reflected portions of the light are passed through a further polarization filter (analyzer), without using immersion oil. Linearly polarized light is radiated onto the skin surface. The portion of the light reflected at the first boundary layer is now also linearly polarized and can be filtered out by correspondingly rotating the polarization plane of the second polarization filter (analyzer) in front of the lens plane of an optical magnifying device. It is thus possible to achieve at least the full ELM effect without using immersion oil. By rotating the second polarization filter located in the beam path of the reflected light, it is also possible to obtain during one examination session both types of display, namely on the one hand the conventional magnifying glass display to assess the surface of the skin, and on the other hand the ELM display which otherwise depends on the use of an immersion fluid. Since also the pigment contained in the pigment cell melanocytes is or contains an optically active substance, the optical impression of this cell population, which is important for the purposes of diagnosis and early detection, can be further enhanced by suitably positioning the analyzer.

As far as the actual design of the new examination device is concerned, two configurations have proved particularly advantageous for routine examinations. One of these provides the image-recording device and also the illumination device in the vicinity of the observation area, while the other locates the illumination device and also the image-recording device at a distance from the skin in order to minimize the thermal stress on the patient's skin.

The preferred type of image-recording device is a small or miniature video camera.

Modern polarization foil filters, which take up very little space, are the preferred polarization and analyzing devices. For special purposes, the planar configuration of the transparent plate which closes off the housing can be dispensed with and a slightly convex or concave plate may be used instead.

For reasons of hygiene and cleaning, glass, and in particular a scratch-proof, tough, hardened mineral glass, is preferred as the material for the transparent plate.

An actual advantageous embodiment of the new compact examination device possesses a high degree of operational flexibility, safe manipulatability and compatibility with the topography of the body. In addition, it complies to a high degree with the nowadays very necessary trend towards miniaturization.

It should be stressed here that modern ribbon cable technology is particularly preferred for the wiring. Modern (personal) computers have proved reliable as control, switching and data storage units, using modern high resolution screens for image reproduction; in particular, trackballs and microswitches or micro-buttons are especially preferred as regulating and control units, and they have proved reliable in medical practice.

Optimal illumination and thus optimal observation conditions are very important, in particular also with regard to reproducibility even after long intervals of time. Uniform scattering of the light can preferably be achieved by roughening the surface of the light-scattering prism.

One preferred embodiment ensures to a high degree that the analyzer is freely rotatable, while at the same time providing a highly stable housing, and thus highly accurate observation conditions are guaranteed.

A multi-part configuration of the housing is advantageous in particular for cleaning and disinfection.

A configuration of the new skin examination device with an offset analyzer-polarization filter has proved particularly advantageous for accommodating the essential functional elements and controls in the smallest possible space.

Another variant of the new device corresponds to the above mentioned second fundamental configuration having functional elements and controls in the handle section. As regards luminous efficiency, a reflecting mirror is preferred as the light-reflecting element. A light guide tube, coated eternally and internally with light-reflecting material, reduces any undesired losses of luminous efficiency.

Another embodiment of the new device is particularly suitable for permitting rapid changing and replacement of light bulbs. Incandescent bulbs of conventional design are cheap and easy to obtain and are therefore the preferred light emission elements.

The above-mentioned relocation of the illumination device such that the skin is exposed to minimal thermal stress can be achieved by means of a further embodiment.

Another embodiment of the new examination device also guarantees miniaturization, which is important in this case, while at the same time ensuring that the equipment is robust.

Reliable electrical contact between the individual modules of the new equipment items, even after the equipment has been dissassembled and reassembled, e.g. for servicing purposes, is guaranteed by another embodiment; this configuration also saves space.

From the standpoint of equipment safety, it is particularly advantageous to ensure that the camera power supply and the other wiring and functional elements and controls are electrically separated from each other.

A variant of the device is particularly cheap to build and is equipped with only one commercially available, easy-to-change incandescent bulb; said variant is equipped with a robust optical system as well as a simple image-recording device.

The use of just one incandescent bulb, e.g. a halogen type with a 10 mm socket, eliminates calibration problems and permits simple, cheap replacement. The production costs are reduced when rotationally symmetrical components are used.

The technical features provided in another embodiment, in particular the offset mounting of the video chip in the camera assembly, make for a particularly advantageous compact structure. A simple setting screw has proved particularly advantageous as the adjusting element.

Further embodiments of the new examination device are particularly kind to the skin and are patient-friendly.

Another essential object of the present invention is a new procedure for optically examining human skin, especially for the reproducible detection and examination of pigmented skin lesions, preferably using a skin examination device of the type described above, A three-stage sequential technique according to another embodiment has the advantage of comprising both analysis and diagnosis, while far exceeding the information content achievable by immersion techniques, and thus considerably enhancing the reliability of the assessment.

An embodiment of the procedure provides for particularly uniform illumination of a skin site to be examined and thus permits less complicated evaluation of the image information.

A distance-controlled, automatic shut-off system for the light according to another embodiment guarantees minimum stress on the patient.

The new diagnostic system can be advantageously used, in particular for training purposes, to display a sample lesion on the screen in the course of a teaching routine, and the observer can be asked to give a diagnosis and criteria. A second screen displays the agreement between the result given by the examining person and reality. In order to end this optional comparison mode, each of the displayed screens can be turned off via a shut-down control panel.

The editing and data management functions contain the options "find" and "update" the text data or "find" and "delete".

A computer-supported diagnosis of pigmented skin lesions can advantageously be set up in principle as follows: There is one fundamental question to be answered by ELM: Is the lesion in question benign or malignant, i.e. should the pigmented lesion be surgically excised or not? It is known from current literature that the sensitivity, i.e. the correct detection of malignant lesions, is in the order of 70%, particularly if the lesion in question is in an early stage. Experts can improve on this sensitivity by approximately 15%.

For all the reasons stated, it is extremely desirable to have available a system which supports the diagnosis made by inexperienced users and which can thus improve the early diagnosis of melanomas. Since the new procedure digitizes image data using video and computer systems, the aim was to develop a new image-processing model as a diagnostic aid.

The functioning of this method is briefly described in the following. It should be stressed that the diagnostic support method described here is based on simple, standard image-processing procedures, and therefore the functioning of the individual procedures will be dealt with only briefly in each case. What is important is the sequence and selection of the individual algorithms or the selection of the extracted features.

An object detection system, which reduces the error rate, and which is largely automated and thus objectivized, operates essentially as follows, using multi-phase segmentation or local formation of threshold values, as well as image data reduction, within the framework of the present invention.

The pigmented lesion is reliably detected as a separate entity from the surrounding skin by means of multi-phase segmentation or by local threshold value formation. A colored image is not necessary for this purpose. A black-and-white image from the red+green channel, e.g. of the video system, is sufficient. In the method used here, the image is reduced to 10 grey values, with the highest grey scale 10 representing healthy skin and the lowest grey scale 1 the darkest site on the pigment lesion. In this way a very coarse image is obtained of the lesion, although the outline of the lesion is accurate, and of the surrounding skin. It is a particular advantage of this procedure that the lighting does not have to be exactly calibrated because only relative variables are processed.

In a masking step, the image-data-reduced lesion is automatically masked.

Using a binary image of the total lesion, the following parameters are determined: Area, circumferential dimension, axial orientation, i.e. symmetry, fractal dimension of the boundary, also aspect ratio.

The margin of the lesion is assessed as follows: Because the boundary of a pigment lesion can provide a great deal of information about the malignity of the lesion, the margin is assessed in such a manner that a binary image is produced from the grey scales 9, 8 and (8+9), and this binary image is analyzed to determine its area in relation to the total area, circumference and fractal dimension.

In order to assess the color and color distribution, the image is transferred via formulae from the RGB-color region (red-green-blue) to the HSI-color region (hue-saturation-intensivity). In the HSI image, the coloration of the object is represented by a per definition black-and-white image. This image, as well as the variation in the distribution of the grey values, provide information on the variability of the coloration, The data are then evaluated via a neuronal network in the following manner: Using the method described above it is possible to significantly reduce the volume of data contained in an image; nevertheless, there are a very large number of parameters which are not available to the diagnostician for assessment because they are so numerous. A wide range of multi-variant procedures can be used for evaluation purposes in order to arrive at a sensible, informative and also sensitive classification. The most suitable method for this purpose has proved to be the use of a neuronal network which has already been confronted by several hundred training data of known diagnoses according to the pattern described below. Advantageously a so-called "back-propagation" algorithm is used. In this way, even when running on a PC, already trained networks can arrive at the appropriate diagnosis with the aid of the aforementioned data within just a few seconds.

An actual lesion is classified into one of the following possible diagnostic categories: (1) unsuspicious lesion; (2) suspicious lesion—it is recommended that it be examined by an expert in pigment lesions; (3) probably malignant lesion—excision and histological examination required.

The sensitivity achieved with such a system or method so far is more than 70%, i.e. more than can be achieved by a human being.

Using an evaluation and diagnostic module of the kind described above, and in the described manner, it is actually possible to achieve an improvement in diagnostic accuracy. Through the interaction of devices and methods operating with polarized light, the simple archiving of pigment lesions, the opportunity to compare images of archived lesions, and through the assessment of pigmented lesions by the machine itself, it is possible to significantly improve the early detection of malignant melanomas and thus to make a major contribution towards reducing the mortality rate caused by this now very frequent tumor.

As regards the computers and monitors used in the concrete, practical examinations leading to this invention, the following remarks can be made.

Computers: A customary commercial computer meeting industry standards (EBM compatible) is used. The basic requirements are for a 386 and 486 microprocessor, at least 4 NB RAM, as well as 3 free 16-bit slots. The hard disk should have a capacity of at least 250 MB.

Monitors: VGA monitor, customary commercial type.

Required additional hardware includes a frame-grabber card in order to process the incoming video signals. The frame grabber cards are commercially available and are used without modification. Two products were tested.

1. The Video-Blaster frame grabber under Windows.

2. Mi(k)ro Movie pro frame grabber under Windows.

The software is written in Visual Basic 3.0 under Windows and contains the following features:

1) patient documentation and archiving 2) image documentation and archiving 3) output of findings An "actual case" will be described in order to bring out clearly the function of the software. Thanks to the special design of the control and archiving software, it should be possible for the operator (doctor) to digitally record and store several lesions and to assign them to the respective location on the body of the patient, without having to stop to input data via the keyboard of the computer. However, at the start of an ELM examination, it is not yet clear how many lesions will be examined or documented.

Description of the sequence of procedures:

1. Start of the examination (screen 1)

The personal data of the patient are recorded (and compared with the existing data). A check is carried out to see whether the patient has already been documented. Each recorded image (file) is thus provided with a unique designation which clearly identifies the patient and in addition contains a counter. The assigning of the date takes place automatically via the internal timer in the computer.

2. Transfer of the video camera signal on-line (screen 2) "live-video"

By directly transferring the already digitized signal from the video camera, it is now possible to observe the skin lesions. This direct observation via the monitor is possible until the order to capture the image is given via the microswitch built into the digital incident light camera. A control panel on the screen permits the lesion image of the to be stored on the hard disk.

3. Identification of the location (screen 3) "image storage—location"

The second screen automatically fades out. A reduced-size version of the captured image is displayed on the left half of the screen. On the rest of the screen a digitized frontal and dorsal image of a person is displayed. Using the track ball built into the digital incident light microscope as an electronic pointing instrument, it is now possible to go to the location of the lesion and to fix it by pressing on a microswitch. This assigns the coordinates of this point to the image file, where they are also stored.

4. Repeat routine (screens 2–3)

A control panel on screen 3 permits the display and storage process to be repeated so that other lesions can be displayed and under certain circumstances documented.

5. Additional options

Image gallery for the identified patient, "thumbnails".

The value of digital ELM using the polarization device(s) is derived in particular from the fact that a lesion can be displayed at two or more different points in time. This makes it possible to provide dynamic information about a lesion and thus to reach decisions about the further fate of the pigmented mark, e.g. the development of a melanoma from a dysplastic nevus, Once the patient has been successfully identified, reduce-sized images from the image archives are displayed on the screen, and in addition the lesion and immediately adjacent to it the location are displayed. By clicking on them, this pair of images can be enlarged (screen 3). Via a control panel, the option of comparing the lesions at different points in time can be selected. The display takes place from left to right, using in each case four pairs of images per screen. The display sequence takes place chronologically up to the time of the respective examination. In addition, the images are displayed according to their respective classification status.

Lesions can be compared at two different points in time as follows: After activating a pair of images showing the lesion and the location, the user clicks on a control panel which permits the comparison to be made at two different points in time. For this purpose, the screen is split; the location information (left-hand image) is masked out and the live-video window (right) is faded in. It is thus possible to display an archival image and the recent image of one and the same pigmented lesion, and to compare the two simultaneously. It is possible to capture the image using the microswitch on the digital incident light microscope. The image is automatically stored without interrogating once more for the location because it can be assumed that both locations are exactly the same. In addition, a flag is placed in the file to provide information on the link made between the images at two or more different points in time.

As regards the display of linked images, the procedure is as follows: By placing the flag in the file it is possible to identify images which are linked with each other. In the course of routine display, the lesions are shown as thumbnails. The source is in each case the earliest version of the lesion. By clicking on this thumbnail, it is possible to display the images of this lesion in a temporal sequence (again as thumbnails), and by further clicking or activating it is possible to go to the routine for comparing lesions at different points in time.

Finally, mention should also be made of the option of remote data transmission, mail box and appraisal by experts. The remote data transmission option is used to support the user in particularly difficult cases. With this option, a lesion which is difficult to assess is transmitted in digitized form to a mail box where it can be appraised by experts. The data transmission takes place via a customary commercial modern using the compressed JPEG format as the transmission format for the information. The size of the file in the JPEG mode is about 50 Kb and the time required for data transmission is thus acceptable. The software contains its own menu point for remote data transmission. The desired lesion is clicked on, using a mouse, and the modem is automatically intialized. An additional data panel permits text information to be transmitted.

The following comments should be made regarding a "learning from examples" option, i.e. a case-based consulation system: An essential part of the diagnostic process in ELM is the comparison with cases which have already been clarified. Up until now, it has always been necessary to rely on the memory of the diagnostician and his or her capacity for abstraction. A new optical impression, a new pigmented lesion, is compared in the brain with already known cases. Thus, for the less experienced user, an image comparison system represents a significant simplification of the task, because the system displays and explains on the one hand the new lesion in question, and on the other hand it displays and explains already analyzed and diagnosed cases. The system already has in memory about 200 pigmented lesions (10 megabytes) (for each pigmented lesion the image, the diagnosis and also a listing of the ELM criteria are available).

The sequence of operations is as follows:

activate the image in question activate the comparison option.

The image in question is displayed in reduced size and the following three modes of diagnostic support are available:

Page through the documented reference lesions for a diagnosis:

The diagnostician is asked to diagnose a suspicious case—the machine shows suitable reference lesions on the right-hand side of the screen. It is thus possible to make an optical comparison between the still visible lesion in question and the examples which have already been diagnosed. The diagnosis and ELM criteria for all the reference lesions are documented in a text panel.

Page through the documented lesions for ELM criteria:

Since the diagnostic technique of epiluminescence microscopy is based on analyzing the patterns of ELM criteria, the diagnostician is asked for those criteria which he would like to see as reference samples. The images which contain these criteria are then displayed. Again it is possible to make an immediate comparison with the lesion in question.

BRIEF DESCRIPTION OF THE DRAWINGS

"Atlas": The reference lesions stored in memory are automatically displayed and explained together with the associated text panels (diagnosis, criteria leading to the diagnosis).

FIG. 9 is a schematic detailed view of a relocated illumination device of the kind advantageously provided for a device according to FIG. 8; and the schematic section and schemnatic top view in;

DESCRIPTION OF THE PREFERRED EMBODIMENTS

Figure 1:
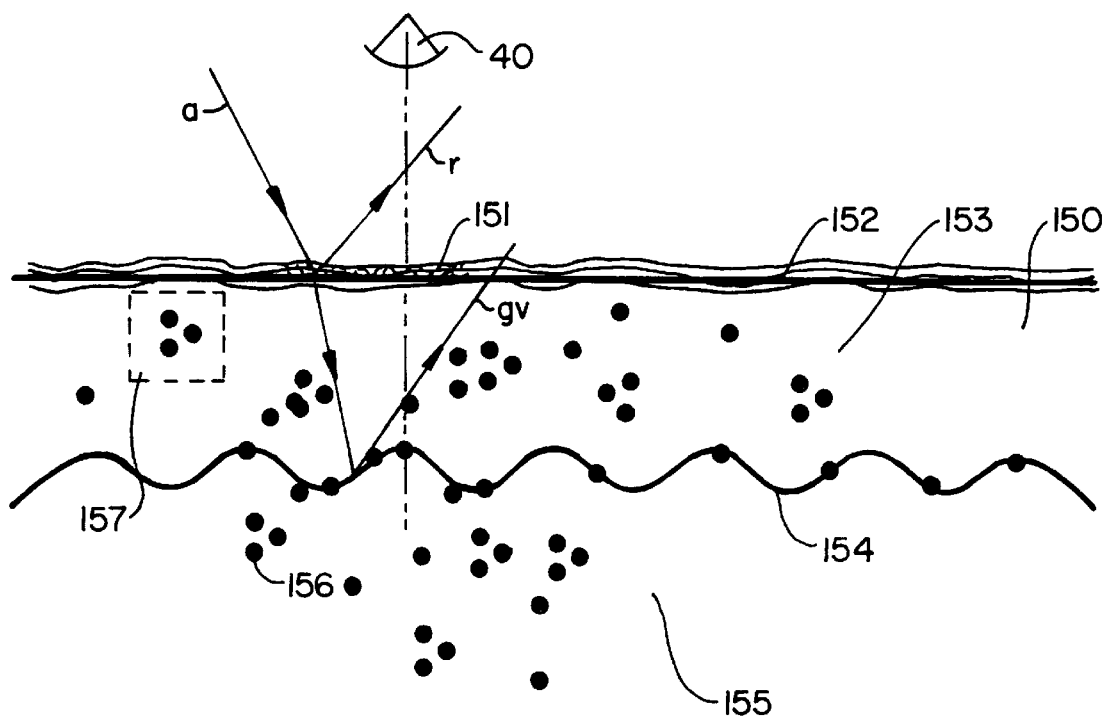
FIGS. 1–4 show in each case a diagrammatic sectional view of the human skin with diagrammatic representations of the techniques used in the past and of the technique according to the invention.

FIG. 1 shows in diagrammatic form a simple method of observing the skin without ELM techniques; it depicts a highly enlarged vertical section through human skin 150 at the observation point 151. The black filled-in circles represent the pigment cells or trelanocytes 156 which form clusters of pigment 157. The arrangement of these pigment cells 156 is characteristic of the disease process in pigmented skin lesions. Three essentially physical boundary layers are important here: a) the boundary layer between the air and the stratum corneum 152, b) the boundary layer 154 between the epidermis 153 and the dermis 155, c) the boundary layer between the pigmented cells 156 in the skin 150 and their surrounding medium. The thickness d) of the epidermis is approximately 0.1–0.3 mm.

The sketch shows the incident light ray a. Most of the light is already diffusely reflected at the uppermost boundary layer between the air and the stratum corneum 152; here the corresponding light ray is denoted by the letter r. A much smaller amount of light, e.g. "gr", is reflected from the other boundary layers. Most of the incident light a is absorbed in the upper parts of the dermis 155.

Therefore, if ELM techniques are not used, it is not possible to see into the epidermis 153, because most of the light has been reflected and far exceeds the quantity of penetrating light, so that very little light from these zones reaches the observer 40, and such light is furthermore completely swamped by the light reflected from the skin surface.

Figure 2:
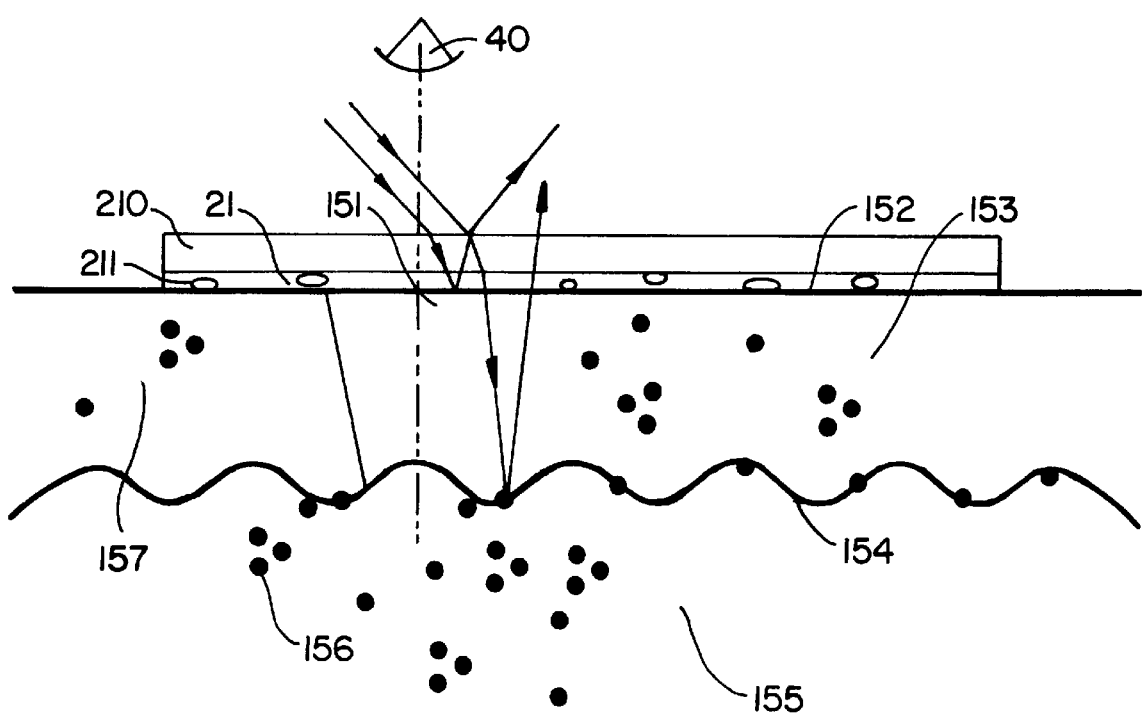

FIG. 2—in which the reference numbers are completely analogous to those in FIG. 1—symbolizes an examination of the skin using conventional ELM techniques. The application of a plane glass plate 210, as well as of a droplet of immersion oil 21 underneath this glass plate 210, reduces the diffusely reflected portion of the light at the uppermost boundary layer. It is now possible to detect relatively more light gr, r, reflected from the deeper-lying portions of the epidermis 153. The essential disadvantage of this method is that the surface of the skin is wetted with oil 21, which causes disruptive reflections, and disruptive air bubbles 211 are formed in the oil film 21, where new boundary layers occur between optically thin and denser media, and these substantially impair observation of a skin site 151 which needs to be examined.

Figure 3:
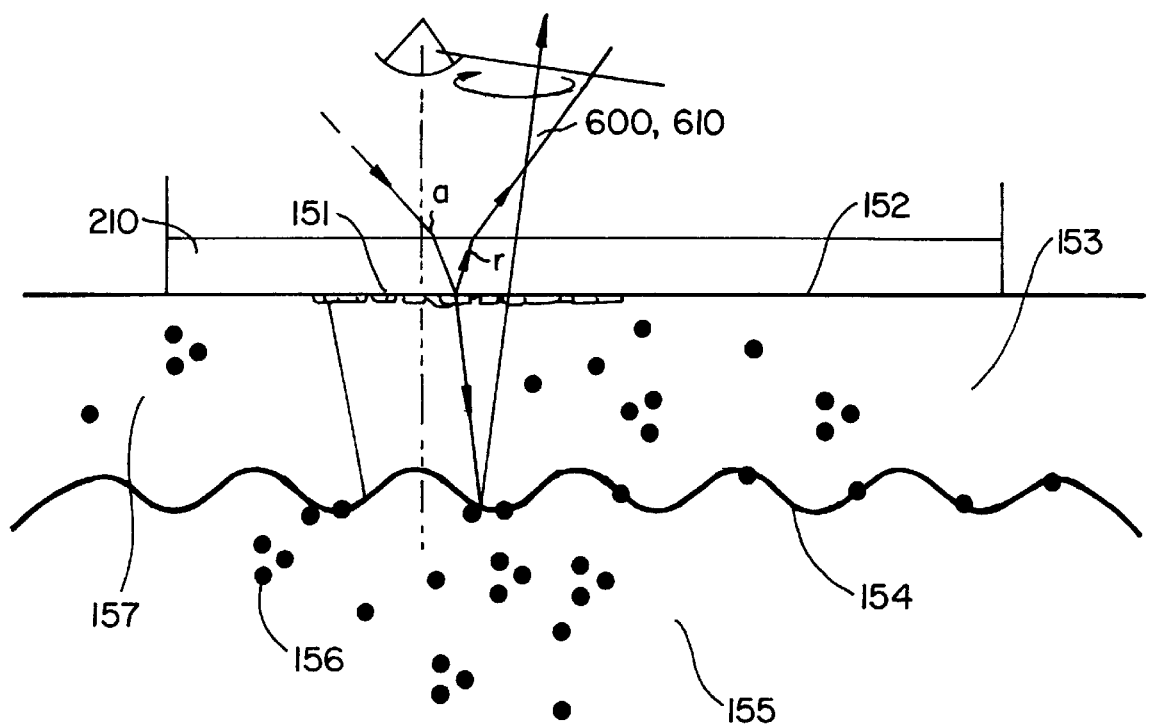

FIG. 3, which also uses reference numbers similar to those in FIG. 1, depicts the method according to the invention for observing skin 150 using a polarization filter 600, 610, namely as an analyzer, without using immersion oil. Light a impinges on the skin surface 151. The amount of light r reflected at the first boundary layer 152 is then linearly polarized and can be filtered out, depending on the polarization plane of a polarization filter 600, 610 (analyzer) positioned in font of the lens plane of a camera or in front of the eye 40. In this way, it is possible, without using immersion fluid, to achieve the ELM effect attained with such fluid. By rotating the analyzer 600, 610 in the direction indicated by the arrow, it is possible to obtain both types of display, namely on the one hand the conventional magnifying glass display to assess the surface, and on the other hand the ELM display, during one examination session. However, this procedure does not permit any relative intensification of the image of the melanin pigment 156, 157, because only a polarization filter 600, 610 is used. This principle is very sensible for routine applications, because relatively more light is available for observing a pigmented lesion.

Figure 4:
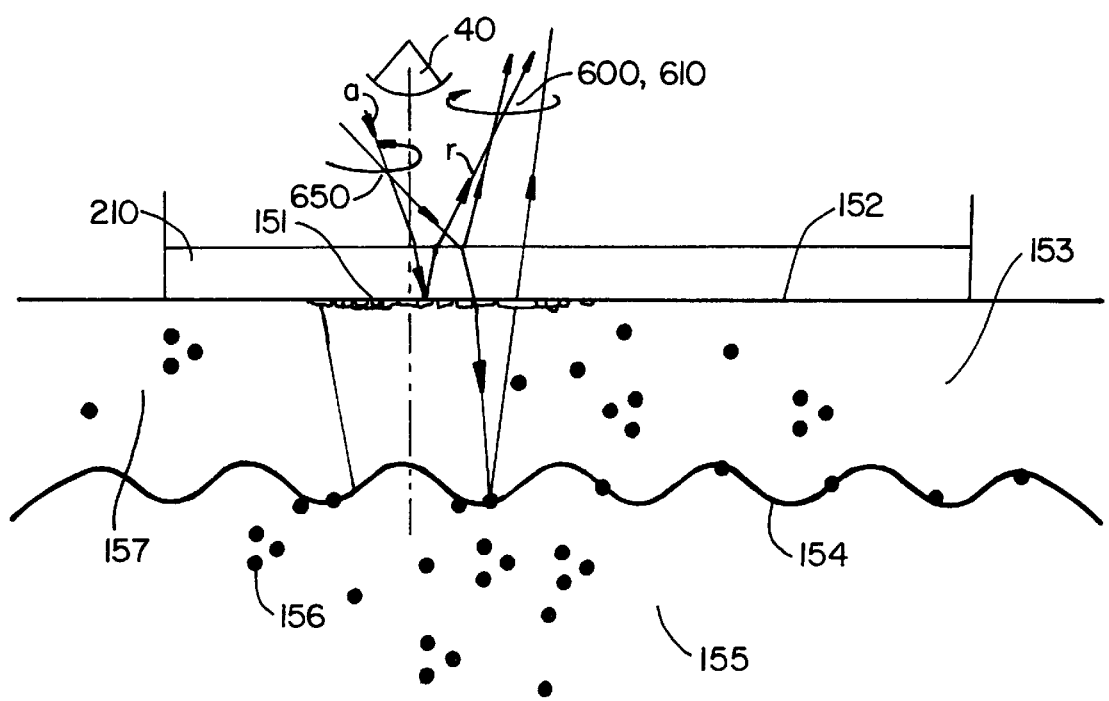

FIG. 4 again uses reference numbers similar to those in FIG. 1, and it shows the skin being examined in the manner according to the invention, using two polarizing devices 600, 650 without the need for immersion oil. With 650, linearly polarized light a impinges on the skin site 151. The amount of light r reflected back from the first boundary layer 151 is now also linearly polarized and can be filtered out depending on the polarization plane of a second polarization filter or analyzer 600 arranged in front of the lens plane or the eye 40. It is thus possible, without using immersion oil, to achieve the ELM effect. By rotating the second polarization filter 600, it is also possible to obtain both types of display, namely on the one hand the conventional magnifying glass display to assess the surface, and on the other hand the ELM display, at one examination session. Since the pigment contained in the pigment cells (melanocytes) 156, 157 is an optically active substance, the optical impression of this population of cells can be further enhanced by suitably positioning the analyzer 600.

Figure 5:
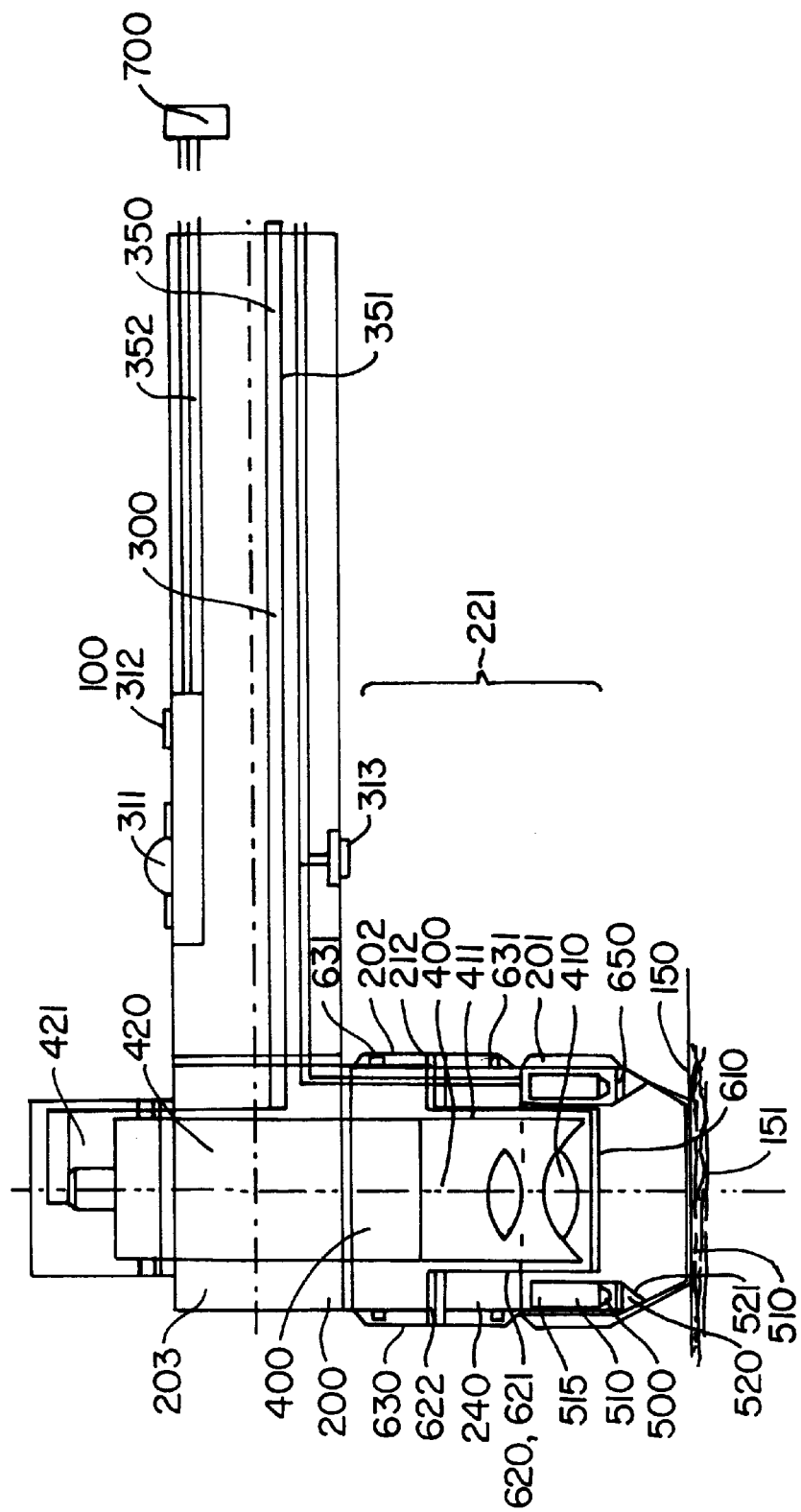
FIG. 5 shows a sectional view of a preferred embodiment of the examination device according to the invention.

The compact device 100 shown in FIG. 5 for examining human skin 150 at a desired site 151 possesses a housing 200 having a front housing section 201 bearing a front plate 210 made of transparent material and adjoining and in alignment with this front section a rear housing section 202 (both housing sections 201, 202 together form a rotatable housing section 221), and the 22 housing base section 203. At the base 203 of the housing, a housing extension 300 projects at right angles radially from the housing 200, and through this extension run power supply, data, signal and control lines 350, 351, 352 which are controllable and switchable by means of switching elements 310—track ball 311, microswitch 312 and micro-button 313—and from here power supply lines 351 run to an optical image-recording device 400 and to an illumination device 500 in housing 200, and at least one control line 352 runs to an external control, image reproduction, image storage, documentation, archiving and/or diagnostic device, preferably to a computer 700, with screen or display, programmed for at least one of the above-mentioned functions.

A microvideo camera 400 with a lens section 410 mounted in the lens housing 411 is arranged centrally and axially in the housing 200 as an image-recording and observation device, together with the camera mount 420 and the end-stage of the camera 421, which projects beyond the housing 200. In the front section of the housing 201, in the annular space 240 between the wall of the housing section 201 and the lens housing 411, is arranged an illumination device 500 comprising a plurality of light emission elements, in particular miniature incandescent bulbs 510, and a holder 515 made of transparent plastic material carrying said elements. Towards the optical opening with the transparent plate 210, this illumination device is adjoined by an annular prism 520 having a slanting, roughened inner surface 521 serving as a light diffuser, said prism being provided on its upper surface, optionally or selectably, with a polarization foil or a controllable polarization device 650 which, if desired, can be used to generate light vibrating in any required plane to be beamed onto the skin site 151 which is to be examined. In order to analyze, or to attenuate, or to perform other similar operations on, in a controlled manner, the at least partially polarized light reflected from the skin site 151 and thereby provide an image of the said skin site, before it enters the enlarging lens 410 of the video camera 400, a polarization foil 610 of a polarization device 600 is arranged in front of the said lens. The polarization device is held by a cylindrical projecting section 621 of a rotatable support 620 for the polarization filter or analyze, which projecting section fits over the housing of the camera lens 411. From this projecting section 621, an annular section 622 extends outwards—here at a right angle—through an intermediate space 212 between the front 201 and rear 202 housing sections. Said annular section is engaged peripherally by a coupling sleeve 630 fitting over both the said housing sections 201, 202, which sleeve is provided with an outer surface suitable to permit rotatory manipulation. The said coupling sleeve 630 is in turn rotatably-slidingly mounted by means of a type of groove and key construction 631 on the outer sides of the two cylindrical housing sections 201, 203.

In the actual embodiment depicted, the housing 200, with the projecting end-stage of the camera 421, has an overall height of 81 mm and the housing extension 300 has an overall length of 131 mm.

Figure 6:
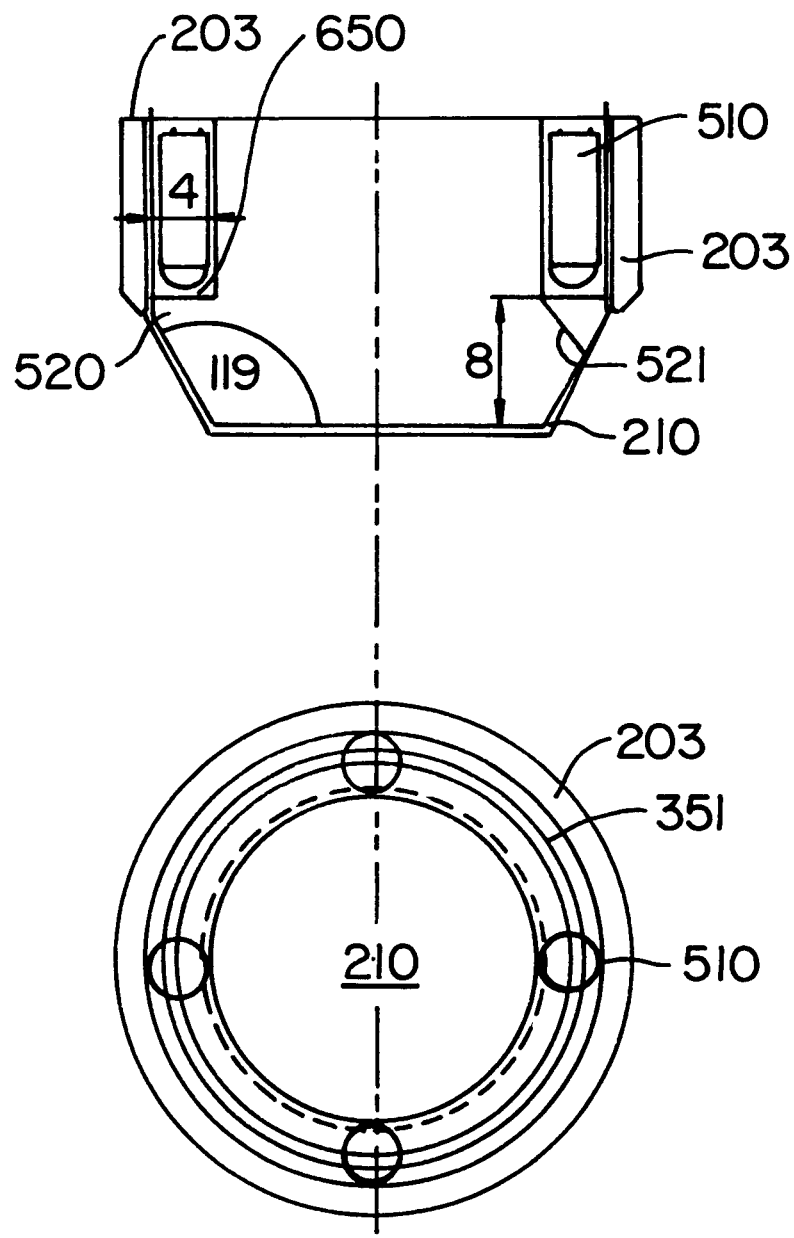
FIG. 6 is a diagrammatic front view of the front section of the housing of the unit depicted in FIG. 5.

Using otherwise the same reference numbers as in FIG. 5, FIG. 6 shows in detail how a substantially hollow-cylindrical illumination device holder (515), made for example from transparent plastic, is arranged in the housing front section 201 having a front plate 210, in such a way that it adjoins peripherally the inner wall of the housing; four 4.5 V halogen miniature incandescent bulbs 510 are positioned in four uniformly distributed recesses in this holder. Below and in alignment with this illumination device holder 515 there follows an annular-shaped incident light polarizer 650 and an annular prism 520 with a roughened light emitting surface 521. In the view from below, the wiring 351 supplying power to the electric incandescent bulbs can be seen.

Figure 7:
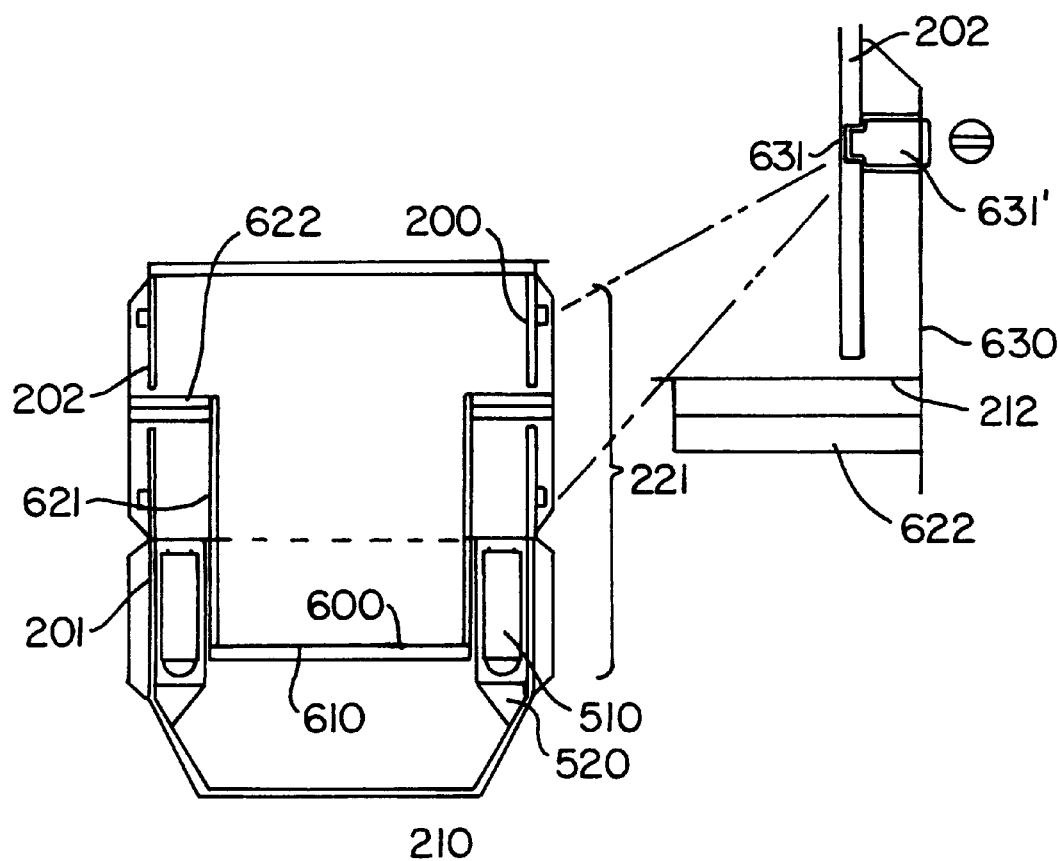
FIG. 7 is a diagrammatic detail of the sliding-rotating mounting of the coupling sleeve of the housing, carrying a polarization analyzer, on a device according to FIG. 5.

The details of the "rotatable" attachment of the outer coupling sleeve 630 of the analyzing device 600, as illustrated in FIG. 7, show the groove and key construction of the rotating-sliding mounting 631 of the coupling sleeve 630 on the outer surfaces of the housing sections 201, 202; here a simple grub screw 631' is used as the "key". The other reference numbers appearing in this Figure require no further explanation because they are similar to those used in FIG. 5.

Figure 8:
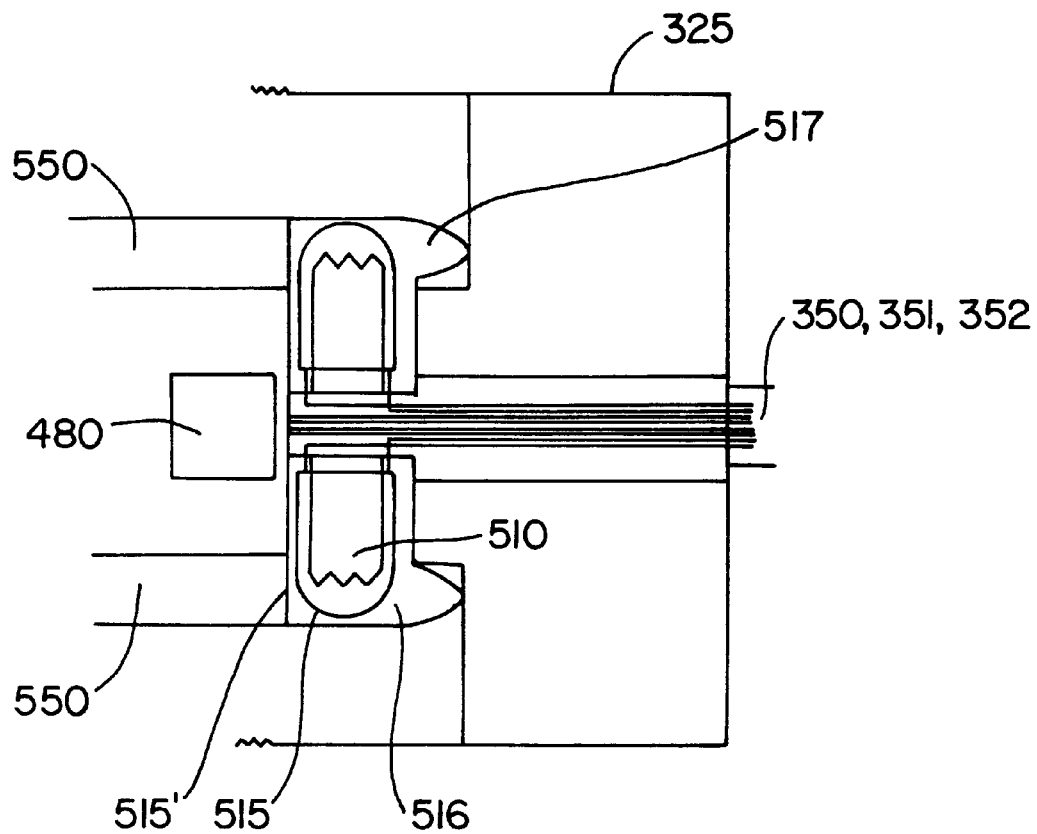
FIG. 8 is a sectional view through a further advantageous embodiment of the examination device according to the invention.

The variant of the new skin examination device 100 according to FIG. 8 differs only little in principle from the device depicted in FIG. 5; it possesses a particularly "low", vertical housing 200 and the housing extension 300—which is also designed as a handle—in this case accommodates the optical image-recording device, i.e. a video camera 400 with a lens or enlarging lens 410 and an illumination device 500 having radially arranged miniature incandescent bulbs 510 in recesses 516 of a transparent holder 515 with reflectors 517 for parallel alignment of the light beams. The end section 325 of the housing extension containing the illumination device 500 is detachably connected to the remainder of the housing extension and possesses contact pins 357 for at least the switching and control lines 352 of the switching and control element 310 with track ball 311 and microswitch 312, and said contact pins cooperate with corresponding contact elements 356 in the remainder of the housing wetension 300 to make connection between the various lines. The control lines 352 lead to a control, switching, image signal, reduction, processing, reproduction, storage, documentation and/or archiving device 700, in particular a computer with screen, display, loudspeaker or similar. The end surface 515' of the illumination device holder 515 fits tightly against the light-conducting and emitting device 550, which is manufactured for example from plastic, in particular from Plexiglas, and coated with reflective material 551, and which extends here in tubular fashion, with an elbow section, into the housing 200.

At the transition from the housing extension 300 into the housing, a reflector 560 is arranged to reflect the image of the skin site into the video camera 400.

A rotatable support 620, which with the transparent plate 410 closes off the housing 200 to the skin 150, is provided for the polarization analyzing 600. The plate 410 is connected with a coupling sleeve 630, which is again rotatably-slidingly mounted by means of a groove and key arrangement 631 on the outer surface of the housing. The annular disc-shaped section 622 of this coupling sleeve possesses a downward-oriented anti-glare device 640 and and an upward-projecting tubular section 621 to which the polarization foil 610 of the analyze is attached.

The other reference numbers appearing in the FIG. 8, which are not further explained here, are the same as those used in. FIG. 5.

Figure 9:
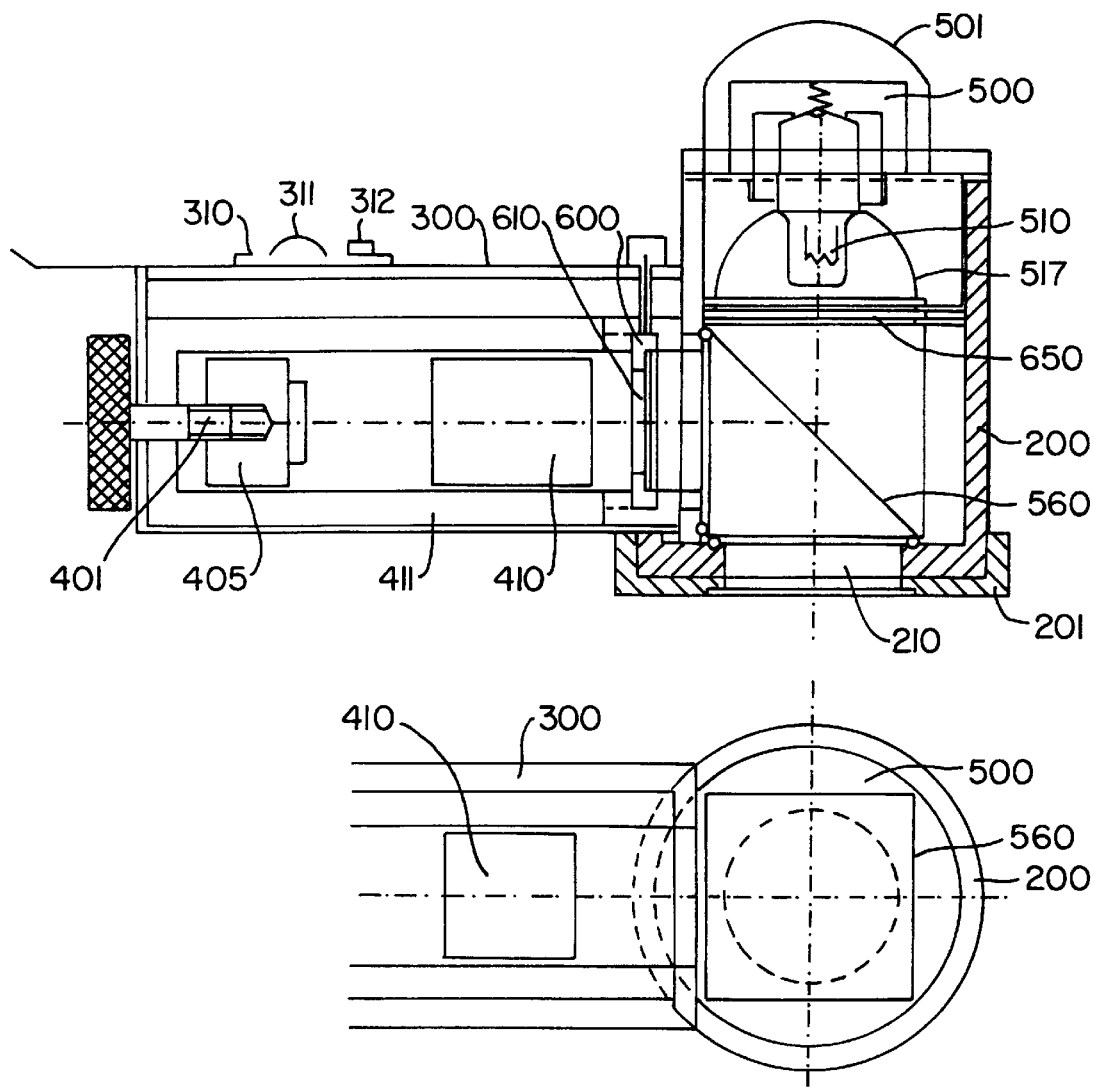

FIG. 9—which uses similar reference numbers to those in FIG. 8—shows the illumination device 500, housed in the end section 325 of the extension of the housing, which can be unscrewed from the housing (not shown here). Said illumination device possesses central power supply and control lines 350–352 and a transparent holder 515 with recesses 516 for spring-mounted incandescent bulbs 510. The end surface 515' fits tightly and without any loss of light against the tubular light guide 550, inside which is mounted the adapter 480 of the video camera (not shown here). In the free space remaining behind the illumination device it is possible to house, for example, some of the electronics for the pointing device and control system.

In the old technology described at the beginning, immersion oil is used to reduce the amount of light reflected from the surface of the skin. As shown, the same principle can be obtained by using double-polarized light. A polarization filter can be optionally mounted or inserted in front of the exit opening from the light source, and a rotatable polarization filter is mounted in front of the inlet opening to the lens of an image-recording device. The amount of light entering the lens is now thus regulatable. The portion of the light polarized by reflection can be eliminated by using filters. This arrangement makes it possible to observe the pigmented skin lesions with and without the known ELM effect. Tests conducted with a prototype have shown that not only can the ELM effect be achieved with this technique, but also the quality can be considerably exceeded.

It is appropriate to add the following remarks regarding the structure and functioning of the devices illustrated in FIGS. 5 and 8, or regarding the functional aspects of the image-recording device used in them:

The image-recording device 400 comprises a video camera with a micro-lens which supplies a video signal via a cable. The image-recording device is supplied with power via another cable.

The analyze 600 or its polarization filter 610 is used to exploit the described physical effect of eliminating disruptive reflections. The analyze is located in the housing 200 and is engaged by a cylindrical projecting section 621. A design using a coupling sleeve 630 permits the projecting section and thus the analyze filter 610 to be rotated as desired.

The front housing section 201 serves as a spacer unit and thus maintains the correct focus to the light-sensitive element or sensor 400. A high pitch thread permits the focus to be adjusted. The glass plate 210 which seals off the device keeps the object to be recorded, namely the skin 150, flat and prevents any foreign bodies from entering the device. For hygienic reasons, the glass plate 210 is designed to be replaceable.

The illumination device 500 provides the illumination of the area to be examined 151. The light sources used are commercially available miniature halogen bulbs 510. This illumination device 500 can be housed axially, i.e. in the housing section 200, as well as in the extension 300 of the housing, with handle, below the light conductor 550. Optionally, in both cases, the light can already be polarized at the time when it is emitted.

A light control system can be provided to protect the light sources and to reduce the thermal stress on the patient's skin: A permanent, weak light source emits light, a phototransistor with circuitry recognizes when the device is approaching the patient's skin or the contact of the glass plate causes the LED light to be reflected and switches [off] the current supply to the bulbs.

The following arrangement can be provided in a second variant: A circuit is incorporated into the serial mouse cable and recognizes signals from the track ball 411 or microswitch 412; an electronic timer circuit switches the power off when no mouse movement signals are received, i.e. when the system remains inactive during the examination process.

A pointing device for the serial computer interface can be housed in the handle 300. It is thus possible to operate the program with the incident light microscope.

A computer program which can advantageously be used for "live" examinations, storage and comparison of the recorded images at different points in time receives the image information via a video digitizing card. The program is designed in such a way to process the signals of the pointing device that the doctor is spared the cumbersome procedure of operating the customary keyboard. All functions—with the exception of the input of personal data—can be remotely controlled from the incident light device.

If a computer program is provided for independent assessment of the recorded pigment lesions, then by using image-processing methods a pigment lesion can be automatically recognized as an object of interest; it can be analyzed according to a wide range of criteria and it can be compared with data from a neuronal network. In this way it is possible to obtain a computer-supported classification or diagnosis.

The actual individual specifications are preferably as follows:

ELM equipment: camera travel: +/−2.5 mm; rotational range of the analyze: >180°; effective field of view: 10 mm; light sources: 4×1.5 V or 4.5 V incandescent bulbs (dimensions 5 by 3 mm); front panel: mineral glass; computer programs: programming language: visual basic or C or C++.

As far as the video camera used is concerned, the following remarks apply:

A miniature video camera manufactured by Panasonic and having a diameter of 15 mm and a length of 25 mm has proved particularly suitable in practice. The resolution is 780×640 pixels and PAL is available as the signal. All video cameras which meet at least these structural and technical requirements can be used. The power supply to the camera is electrically separate from the rest of the system.

The lens is also a commercially available unit and achieves a field of view of slightly more than 10 mm in diameter. The resulting field of view is smaller than the field of view of the lens and uses only the central, optically high-grade portions of the lens.

Figure 10:
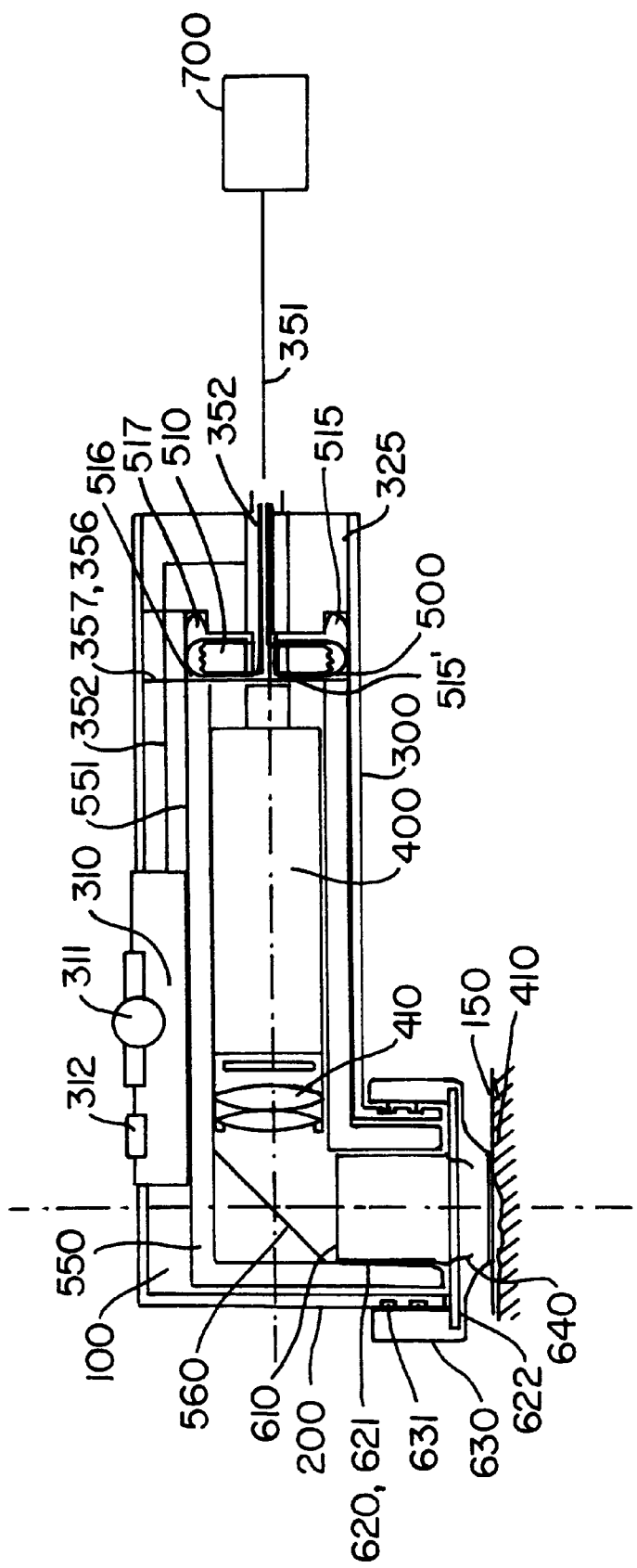
FIG. 10 represent a particularly robust and economically manufacturable variant of the new examination devices.

The cost-effective variant of a device according to the invention, which is shown in sectional view and top view in FIG. 10, possesses a relatively short—in this case hollow cylindrical—housing 200 closed off at the bottom by a push-on end cap 201 and a glass plate 210. From this housing an extension 200, which is also hollow-cylindrical in shape and is externally advantageously configured as a manipulating handle, projects at a right angle and carries a switching and control element 310 with track ball 311 and microswitch 312, for switching and controlling an external control, reproduction and/or storage device, in particular a computer (not shown here). In the geometrical opening between housing 200 and extension 300, a two-part cube prism 560 is arranged directly behind the glass plate 210 as a light-conducting and light-reflecting element, and further along the optical axis of the housing 200 are arranged a—in this case fixed—polarizer 650 and an illumination device 500 with a housing 501 and an incandescent bulb 512, as well as a parabolic refector 517. Along the optical anus of the extension 300 of the housing, starting from prism 560, the following units are arranged: A rotatable analyze with polarization foil 610 and, in a support 411, an optical lens system 410 as well as a video sensor 405 of an optical image-recording unit 400, and the focus of the said video sensor can be adjusted by means of the setting screw 401.

This variant of the design is characterized in particular by a reflecting prism. By using this prism, orthogonal illumination is possible, while observation is carried out through an offset camera unit aligned perpendicular to the direction of illumination. The structure is in principle the same as in the variants already depicted in the preceding figures.

I claim:

1. A device for optically examining human skin and its pigmentations, the device comprising:

a cylindrical housing;

a substantially planar transparent plate detachably applied to a skin site to be examined without introducing an immersion fluid, the transparent plate delimiting the housing from the skin site, the transparent plate being made of a transparent plastic or glass material;

a vertical light illumination device disposed in the housing and radiating light directed to the skin site along an incident beam path;

an optical observation device disposed in the housing and in the incident beam path, and including an optical enlarging device;

a light-polarizing device disposed in a reflected beam path of light reflected from the skin at the skin site and arranged between the illumination device and the transparent plate, the light-polarizing device including a polarizer for polarizing the incident light beam directed to the skin site along the incident beam path and an analyzer for analyzing the reflected light beam in the reflected beam path from the skin at the skin site, the light-polarizing device being variably controllable to modify the type, degree, and angle of polarization;

an optical image-recording device disposed in the housing;

a hollow housing extension projecting from the housing and acting as a manipulating handle; and at least one regulating, switching and control element disposed outside of the hollow housing extension and coupled to the devices disposed in the housing by lines extending through the hollow housing extension.

2. The device of claim 1 wherein the light polarizing device is variably controllable to be switched on and off or be mechanically moved relative to the incident beam path and reflected beam path.

3. The device of claim 1 wherein the light-polarizing device is arranged between the optical image-recording device and the transparent plate.

4. The device of claim 1 wherein the housing is tubular and has an axis and the optical image-recording device comprises a miniature video camera and a camera lens disposed between the video camera and the transparent plate, the device further comprising at least one polarization filter disposed between the camera lens and the transparent plate, and wherein the video camera, camera lens, and polarization filter are aligned along or parallel to the axis of the tubular housing, the at least one polarization filter being rotatably adjustable about the axis of the tubular housing.

5. The device of claim 4 further comprising:
a lens housing carrying the camera lens and spaced from the wall of the tubular housing by a peripheral annular space;
a transparent plastic holder disposed in the peripheral annular space and including a plurality of illuminating elements; and
a vertical beam-focusing and diffuser element disposed on a main light-emitting side of the transparent plastic holder and including an annular prism made of a transparent glass or plastic material, the annular prism having an angled lower side which is surface-treated to scatter light.

6. The device of claim 4 wherein the housing includes a front housing section, a rear housing section substantially aligned with the front housing section, and an intermediate space defined between the front and rear housing sections, the transparent plate and illumination device being disposed in the front housing section, the video camera being disposed in the rear housing section, the intermediate housing section including a support element holding the at least one polarization filter, the support element having an annular section connected to a rotatable coupling sleeve having a ribbed outer surface which is mounted on outer surfaces of the front and rear housing sections to prevent axial displacement between the front and rear housing sections.

7. The device of claim 6 wherein the housing includes a rotating housing section comprising the front and rear housing sections and carrying the support element which is slidably and rotatably mounted to the front and rear housing sections, the rotatable housing section being detachably connected by a screw thread to a housing base section carrying the hollow housing extension extending therefrom at an angle.

8. The device of claim 6 further comprising a projecting element surrounding and holding the at least one polarization filter and coaxially surrounding the camera lens, the annular section being mounted on the outside of the housing and extending radially from the projecting element, the support element carrying the projecting element and the annular section.

9. The device of claim 4 wherein the illumination device is arranged on a side facing away from the camera lens and the miniature video camera and light is supplied to the illumination device by at least one light-conducting cable leading from an exterior of the housing.

10. The device of claim 1 further comprising an external storage device coupled to the at least one regulating, switching and control element.

11. The device of claim 1 wherein the housing forms a shortened observation head having a coupling sleeve with a ribbed outer surface slidably and rotatably mounted on the outer surface of the housing, the housing carrying the transparent plate and including a support element holding the at least one polarization filter, the hollow housing extension projecting at an oblique angle or a right angle from the housing, the illumination device being peripherally arranged in the hollow housing extension and including at least one light-emitting element, the illumination device having a peripheral light-conducting and light-emitting element which comprises a light-conducting tube having inner and outer walls coated with light-reflecting material or an optical fiber element, the illumination device extending into the housing and surrounding the centrally arranged optical image-recording device, the illumination device further including at least one light-reflecting element for the light reflected from the skin at the skin site.

12. The device of claim 11 wherein the hollow housing extension includes a distal end section detachably connected thereto and the illumination device is disposed in the distal end section, the illumination device including a holder made of a transparent material and having radial recesses for receiving a plurality of replaceable light-emitting elements with parabolic reflectors, the holder having end surfaces that fit tightly against end surfaces of the peripheral light-conducting and light-emitting element.

13. The device of claim 12 further comprising electrical power supply, signal, data, and control lines extending through an end section of the hollow housing extension into the housing extension, and wherein the at least one regulating, switching and control element is disposed at the end section or the housing extension and coupled to the illumination device, the optical image-recording device, and the light-polarizing device via the lines for operating the devices.

14. The device of claim 13 further comprising an electronic control system for the at least one regulating, switching and control element and at least one contact plug unit cooperating in line-connecting fashion with a corresponding contact plug unit in the hollow housing extension, at least parts of the electronic control system and the at least one contact plug unit being arranged in the end section of the hollow housing extension.

15. The device of claim 13 wherein the electrical power supply lines and components of the optical image-recording device are electrically separated from a remainder of the housing and hollow housing extension and from a remainder of the at least one regulating, switching and control element.

16. The device of claim 1 wherein the housing has an optical axis and forms a shortened observation head closed off by the transparent plate which is placed on the skin to be examined, the hollow housing extension projecting at an angle or orthogonally from the housing, the device further comprising a partially light-reflecting and light-transparent, light-conducting and light-reflecting element disposed at a geometrical opening between the housing and the hollow housing extension and directly adjoining the transparent plate, the light-conducting and light-reflecting element further adjoining the polarizer and the illumination device disposed along the optical axis of the housing, the illumination device being detachable and having at least one light emitting element, the hollow housing extension having an optical axis, the analyzer and optical image-recording device being disposed along the optical axis of the hollow housing extension away from the light-conducting and light-reflecting element, the analyzer being rotatably adjustable.

17. The device of claim 16 wherein the light-conducting and light-reflecting element comprises a cube prism or a semi-mirrored transparent plate, and the illumination device includes a reflector.

18. The device of claim 1 further comprising a video sensor, a camera electronic system, a positioning element, and a lens disposed in the hollow housing extension which has an axis, the video sensor being slidingly focusable by the positioning element along the axis of the hollow housing extension.

19. The device of claim 1 further comprising an opto-electronic circuit having a secondary, weakly intensive light emitter for emitting light to the skin and a photosensor which reacts with adjustable intensity to an emitter light reflected by the skin, so that when the transparent plate is moved toward or away from the skin depending on an adjustable distance from the skin, the light needed to illuminate and examine selected sections of the skin is automatically switched on or off, to reduce thermal stress on the skin.

20. The device of claim 1 further comprising a timer which automatically switches off the illumination device when the at least one regulating, switching and control element is detectably inactive for a selected period of time during an examination to reduce thermal stress on the skin.

21. A procedure for optically examining human skin comprising the steps of:
applying a substantially planar transparent plate on the skin to stretch and smooth a skin site to be examined without introducing any immersion fluid;
directing an incident light beam through the transparent plate to the skin site to illuminate the skin site which reflects a reflected light beam;
providing a polarizer for polarizing the incident light beam and an analyzer for analyzing the reflected light beam;
carrying out in combination polarization of the incident light beam and polarization analysis of the reflected light beam;
controlling the polarizer and analyzer to modify the type, degree, and angle of polarization;
separately carrying out polarization of the incident light beam without polarization analysis of the reflected light beam or polarization analysis of the reflected light beam without polarization of the incident light beam; and
storing one or more images of the skin site generated by the reflected light beam.

22. The procedure of claim 21 wherein both polarization of the incident light beam without polarization analysis of the reflected light beam and polarization analysis of the reflected light beam without polarization of the incident light beam are separately carried out.

23. The procedure of claim 21 further comprising the step of optically enlarging the images generated by the reflected light beam.

24. The procedure of claim 21 wherein the reflected light beam includes light reflected from an epidermis and from a junction zone between the epidermis and a dermis of the skin.

25. The procedure of claim 21 wherein the incident light beam is non-polarized, and further comprising the steps of obtaining an image of the skin site by placing a polarization analyzer or a polarizer and a polarization analyzer in combination in the path of the reflected light beam; obtaining another image of the skin site without placing a polarization analyzer or a polarizer in the path of the reflected light beam; and recording the obtained images.

26. The procedure of claim 21 wherein the incident light beam comprises a broadly diffuse, polarized or non-polarized light.

27. The procedure of claim 21 wherein the incident light beam comprises elliptically polarized light.

28. The procedure of claim 21 wherein the reflected light beam is passed through an elliptically polarizing analyzer.

29. The procedure of claim 21 further comprising the step of automatically switching on or off the incident light beam directed to the skin site to reduce thermal stress imposed on the skin by the incident light beam during examination, using an optoelectronic circuit having a secondary, weakly intensive light emitter for emitting light to the skin and a photosensor which reacts with adjustable intensity to an emitter light reflected by the skin, as a function of a selectable distance of the transparent plate as it is moved toward or away from the skin.

30. The procedure of claim 21 further comprising the step of automatically switching off the incident light beam when switching elements for controlling the steps of carrying out polarization and storing the images remain inactive for a selected period of time during an examination to reduce thermal stress on the skin.

31. The procedure of claim 21 further comprising the steps of performing computer-supported processing, analysis, and data reduction of the images and performing comparative detection, addition, or subtraction of image content of the images with documentation storage facilities.

32. A procedure for optically examining human skin comprising the steps of:
applying a substantially planar transparent plate on the skin to stretch and smooth a skin site to be examined without introducing any immersion fluid;
directing an incident light beam through the transparent plate to the skin site to illuminate the skin site which reflects a reflected light beam;
carrying out in combination polarization of the incident light beam and polarization analysis of the reflected light beam;
separately carrying out polarization of the incident light beam without polarization analysis of the reflected light beam or polarization analysis of the reflected light beam without polarization of the incident light beam; and
storing one or more images of the skin site generated by the reflected light beam;
the procedure further comprising the steps of processing an image of the skin site:
(a) separating signals or data of a pigmented lesion from signals or data of the skin surrounding the lesion of the image by multi-phase segmentation or local threshold value formation;
(b) reducing the image to n levels of relative grey values, with level n representing healthy skin and level 1 representing the darkest site of observed lesion of the skin site in the image, and forming an exact outline image of the lesion;
(c) masking the lesion;
(d) forming a first binary image of the lesion and determining parameters of the lesion including an area, circumferential dimension, symmetry, fractal dimension or boundary of a margin, and an aspect ratio;
(e) assessing the margin of the lesion by forming a second binary image from grey stages n−1, n−2, and (n−1)+(n−2) and analyzing the image with regard to relationship of areas of the first and second binary images to each other and circumferential dimension and fractal dimension of the second binary image;
(f) assessing pigmentation by sequential measurement of dark portions of the image;
(g) assessing color and color distribution by transfer of the image from a red-green-blue color region to a hue-saturation intensity color region and display coloration and variability of objects by a per definitionem black-and-white image;
(h) evaluating the reduced data of the image and comparing the reduced data with known data for lesions with known and classified diagnoses using multi-variate procedures employing a neuronal network having at least 100 images; and
(i) classifying the image into one of a plurality of categories of a diagnostic key having several levels that include (1) a non-suspicious lesion, (2) a suspicious lesion, and (3) probably a malignant lesion, and reporting the category detected.

* * * * *